United States Patent [19]

Peyman

[11] Patent Number: 5,767,105
[45] Date of Patent: Jun. 16, 1998

[54] OCULAR SOLUTION

[76] Inventor: Gholam A. Peyman, 8654 Pontchartrain Blvd., Unit 1, New Orleans, La. 70124

[21] Appl. No.: 768,393

[22] Filed: Dec. 18, 1996

Related U.S. Application Data

[63] Continuation of Ser. No. 433,190, May 3, 1995, abandoned.

[51] Int. Cl.$^6$ .................................................. A61K 31/715
[52] U.S. Cl. .............................. 514/53; 514/54; 514/912
[58] Field of Search ............................ 514/53, 54, 912

[56] References Cited

U.S. PATENT DOCUMENTS

| | | |
|---|---|---|
| 4,238,482 | 12/1980 | Peyman et al. |
| 4,443,432 | 4/1984 | Garabedian et al. |
| 4,620,979 | 11/1986 | Schachar. |
| 4,775,531 | 10/1988 | Gilbard. |
| 4,886,786 | 12/1989 | Lindstrom et al. |
| 4,983,583 | 1/1991 | Ridoux. |
| 5,116,868 | 5/1992 | Chen et al. |
| 5,258,412 | 11/1993 | Peyman et al. |
| 5,293,487 | 3/1994 | Russo et al. |

OTHER PUBLICATIONS

W. Keeton, Biological Science Second Edition, pp. 30–31, 42, 174–175 Intravitreal Surgery, Chapter 3, pp. 59–65, 104–105 (1979).
Jicst–Eplus 87015068o Abstract of Journal of Japanese Soc. Hospital Pharmacy (1986).
BioSis Abstract of Invest Ophamol Visual Science 27(11), 1986.

*Primary Examiner*—Zohreh Fay
*Attorney, Agent, or Firm*—Roylance,Abrams,Berdo & Goodman, L.L.P.

[57] ABSTRACT

An ophthalmologic solution containing oligosaccharides in an appropriate concentration. The oligosaccharide preferably is a disaccharide such as sucrose, maltose or lactose. The disaccharide is placed in solution in a pharmacologically acceptable concentration ranging from 0.1% to 11.4%. The disaccharide can be added to physiologic saline, Lactated Ringers, balanced salt solution or other appropriate physiologic solution. The disaccharide does not enter the tissue cells and maintains an extracellular pressure gradient that prevents flow of fluid into the eye. The solution is used to replace vitreous or used topicall. One or more pharmacologic agents or drugs may be added to the solution.

20 Claims, No Drawings

OCULAR SOLUTION

This is a continuation of application Ser. No. 08/433,190 filed May 3, 1995, now abandoned.

BACKGROUND OF THE INVENTION

This invention relates generally to ophthalmologic surgery and, more particularly, to an irrigating and vitreous replacement solution used in intraocular surgery that prevents clouding of the lens and post-surgical cataract formation.

Ophthalmic solutions are known to the art. The most common form of ophthalmic solution is the topical solution. Topical ophthalmic solutions can be used as irrigants, moisturizers, vehicles for topical pharmaceutical preparations and so forth. A less common form of ophthalmic solution is the vitreous replacement solution.

Vitreous replacement solution is introduced into the vitreous cavity of the eye when aqueous humor or vitreous is removed from the eye. This may occur in the presence of vitreous hemorrhage or, more commonly, during a vitrectomy procedure to repair a detached retina. Infusion fluids are usually required to replace vitreous and maintain the shape of the eye.

Ophthalmic solutions, both topical and intravitreal, can affect corneal and lens clarity which affects the results of ophthalmic surgery. Corneal swelling during vitrectomy, for example, is influenced by the components of the irrigating solution and by intraocular pressure. As a result, despite the solution used, the lens may become cloudy as a result of the infusion. It has been found that the use of certain irrigating or vitreous replacement solutions during surgery can induce post-surgical cataract formation.

Generally, the cataract results from the flow of molecules into the lens tissue cells. For example, glucose molecules from the solution actively and passively move into the cells. The glucose molecules raise the osmotic pressure in the cells which draws fluid into the cells. This flow of fluid into the cells causes the lens to cloud. The cells can swell and rupture, further damaging the lens. It is necessary, however, for the nutrition of the cells to have some glucose in the solution.

Researchers have directed their efforts toward developing a physiologic and nontoxic irrigating or vitreal replacement solution. The ideal solution would maintain the physiologic integrity of the eye, would be easy to prepare and remain stable. Few solutions meet these requirements.

There are a number of prior art patents disclosing irrigating and replacement solutions. Among those is U.S. Pat. No. 4,983,585, to Pennell et al, which discloses a viscoelastic irrigation solution for use in eye surgery have a physiologic saline base with about 2% hydroxymethyl cellulose, a long chain polysaccharide, and about 10 ppm polyethylene oxide. U.S. Pat. No. 4,620,979, to Schachar, provides an opthalmological irrigating solution containing ascorbate, glucose, various buffers and electrolytes. U.S. Pat. Nos. 5,298,487 and 5,116,868 to Chen et al provide ophthalmic irrigating solutions of buffered balanced salt solution, antioxidants and glucose. U.S. Pat. No. 4,238,482 to Peyman et al discloses an intraocular infusion irrigation solution having a physiologically acceptable saline solution and an oncotic pressure agent selected from a colloid-type dextran.

It will be appreciated that many of these solutions contain an osmotic pressure agent, generally saline, dextrose or an oncotic agent such as dextran or methylcellulose. Furthermore, many have dextrose required for cell nutrition. Saline can cause severe changes in the lens or corneal permeability. Dextrose has been shown to be more effective than saline in preventing corneal swelling and endothelial damage. Dextran has been shown to inhibit lens swelling is select circumstances.

Glucose flows into the lens actively and passively. Glucose is a monosaccharide, that is, a sugar that cannot be decomposed into a simpler sugar. Glucose, therefore, has a relative small molecular size which allows it to pass through the cell wall of the lens tissue cells either passively or it is actively transported under the effect of the pressure gradient. Even a normosmolar dextrose solution, if left in contact with the lens tissue, can cause cataract formation. Glucose eventually will pass into the cell and draw fluid into the cell causing the lens to cloud and swell.

Since there can be a relatively large number of glucose molecules per milliliter of solution, it is possible to create a hyperosmolar dextrose solution in an attempt to keep a positive pressure gradient outside the lens tissue and inhibit movement of the glucose molecules into the cell. However, a hyperosmolar solution temporarily can dehydrate the lens. It will be appreciated that glucose from a hyperosmolar solution eventually will enter the cell by active transport and cause cells to swell.

By contrast, dextran is a polysaccharide having a relatively high molecular weight. Polysaccharides are complex carbohydrates composed of many simple sugars bonded together in a long chain. Although dextrans do not move into the lens, due to their high molecular weight and resulting viscosity, they do not work as well in intraocular replacement solutions. Dextran solutions should not be used for phacoemulsification or irrigation aspiration of the lens because it would protect the lens and prolong surgery. Furthermore, dextran solutions do not mix well with blood and should not be used in the presence of vitreal hemorrhage. This last disadvantage severely limits the usefulness of dextran solution as a vitreal replacement fluid.

Even balanced salt solution (BSS) has drawbacks. The sodium chloride can enter the cells and cause hydration of the surgical wound. Studies have demonstrated lens opacification when BSS was used during vitrectomy on diabetic eyes. Haimann & Abrams, Prevention of lens opacification during diabetic vitrectomy. OPHTHALMOLOGY. 1982;91:116–121.

It would be advantageous, therefore to have a replacement or irrigation fluid that has advantages of glucose and polysaccharides without their disadvantages. I have determined that a novel solution of disaccharides or other select oligosaccharides works well as intraocular replacement solution and as a topical irrigant or vehicle to carry various pharmaceutical agents. The disaccharide is not actively transported into the cell and thus maintains the osmotic pressure outside the cell to prevent fluid from entering the cell.

The three most common oligosaccharides are the disaccharides or double sugars maltose, lactose and sucrose. The disaccharide's are compound sugars composed of two simple sugars bonded together through a condensation reaction or dehydration reaction that involves the removal of a molecule of water. Sucrose, for example, is common table sugar and is synthesized by a condensation reaction between a molecule of glucose and a molecule of fructose. Lactose, or milk sugar, is composed of glucose and galactose.

It is important to note that a disaccharide breaks down into its component simple sugars by a reaction known as hydrolysis and involves the addition of a water molecule. Hydrolysis of a disaccharide requires the presence of a catalyst or enzyme. Specific enzymes are required for the breakdown of carbohydrates. Enzymes split double sugars into simple sugars. For example, maltase splits maltose, sucrase splits sucrose and lactase splits lactose. It is important to the scope of the present invention to understand that there are no such enzymes in the aqueous of the eye.

SUMMARY OF THE INVENTION

It is a principal object of the present invention to provide an ophthalmologic solution that does not induce cloudiness of the lens or induce post surgical cataract formation.

Another object of the invention is to provide an ophthalmologic solution that contains an osmotic agent that is not transported into the cells.

It is still another object of the invention to provide an ophthalmologic solution that can be used to replace vitreous or used topically.

It is yet another object of the present invention to provide such an ophthalmologic solution that can function as a vehicle for various pharmacological agents such as antiinfectives, antiinflammatories and anesthetics.

A further object of the present invention is to provide such an ophthalmologic solution that is easy and economical to make, stable, easy to use and well suited for its intended purposes.

In accordance with the invention, an ophthalmologic solution is provided consisting of an oligosaccharide in an appropriate concentration. The oligosaccharide preferably is a disaccharide such as sucrose, maltose or lactose. The disaccharide is placed in solution in a pharmacologically acceptable concentration ranging from 0.1% to 11.4%. The pH and osmotic value of the resulting solution is compatible with the eye. The disaccharide can be added to physiologic saline, Lactated Ringers, balanced salt solution or any other appropriate solution. The disaccharide cannot be actively transported into the cells and maintains an extracellular pressure gradient that prevents flow of fluid into the cells.

The resulting solution is used to replace vitreous or used topically on the eye. One or more pharmacological agents in pharmacologically acceptable concentrations may be placed in the solution. Such agents include, but are not limited to antibiotics, anti fungals, antiinflammatories, anesthetics, and vasoconstrictors.

DESCRIPTION OF THE PREFERRED EMBODIMENT

The ophthalmologic solution of the present invention is comprised of an oligosaccharide in solution. The oligosaccharide preferably is a disaccharide such as sucrose. The solution preferrably is a normosmolar or hyperosmolar solution of the disaccharide in water as a sufficient concentration of disaccharide resulting in an acceptable pH and osmotic pressure. The disaccharide also can be placed in physiologic saline, Lactated Ringers or balanced salt solution or any other acceptable solution.

EXPERIMENTAL RESULTS

1.Evaluation Of Electroretinogram Changes After The Administration Of Sucrose Into The Vitreous Cavity
Materials and Methods:
Animals:
Twelve New Zealand white rabbits of 2 to 3 kg were maintained at 20° C. on a daily lighting schedule of twelve (12) hours dark and twelve (12) hours light. All experiments were conducted with the ARVCO Resolution on the Use of Animals in Research. Two to four rabbit eyes were used for each tested group.
Materials:
The disaccharide sucrose (F.W. 342.30) was purchased from Mallinkrodt Specialty Chemicals Co., Paris, Ky.
Solutions:
The solutions in Table 1, were prepared by mixing sucrose in sterile distilled water and tested for pH value and osmotic pressure to predict the pH effect and osmotic effect on a physiologic solution. Osmotic pressure and pH value of the following sucrose solutions were measured by using a vapor pressure osmometer and a pH meter.

TABLE 1

| | pH value | Osmotic pressure |
|---|---|---|
| Concentration (sucrose) | | |
| 0.10% (0.1 g/100 ml) | pH 6.0 | 0.077 M |
| 1.0% (1 g/100 ml) | pH 6.0 | 0.090 M |
| 4.0% (4 g/100 ml) | pH 6.2 | 0.140 M |
| 8.0% (8 g/100 ml) | pH 6.11 | 0.290 M |
| 11.4% (11.4 g/100 ml) | pH 6.15 | 0.450 M |
| Control solutions | | |
| Distilled water | pH 6.0 | 0.076 M |
| BSS | pH 7.2 | 0.305 M |

Surgical Procedure:
The animals were deeply anesthetized using an intramuscular injection of ketamine hydrochloride (50 mg/kg) and xylazine hydrochloride (5 mg/kg). The eyes were dilated with drops of both tropicamide 1% (Mydriacyl, Alcon Laboratories, Fort Worth, Tex) and cyclopentolate hydrochloride 1% (Cyclogyl, Alcon Laboratories, Fort Worth, Tex). Approximately 0.2 ml of aqueous humor was aspirated from the anterior chamber by using a 30 gauge needle mounted on a 1 ml syringe. The needle was inserted through a small puncture in the peripheral cornea under an operating microscope.

A 30 gauge needle was connected to a tuberculin syringe containing 0.2ml of solution of the present invention. The solution of the present invention was prepared by adding the appropriate amount of sucrose to an appropriate volume of physiologic solution. The physiologic solution had the following formulation (g/L):

| | |
|---|---|
| NaCl | 3.26 to 6.521 |
| Dextrose | 0.901 |
| KCl | 0.359 |
| $CaCl_2$ | 0.115 |
| $MgCl_2 6H_2O$ | 0.159 |
| $NaH_2PO_4$ | 0.103 |
| $NaH_2CO$ | 2.454 |
| pH | 7.40 |
| Osm | 153 to 306 |

The sucrose concentration of various tested solutions ranged from 0.1 % to 11.0%, each solution having a pH of approximately 7.0 to 7.4. The osmotic pressure of the test solutions was calculated as additive for the osmolality of the sucrose solutions shown in Table I and the physiologic solution and, therefore, ranged from 230 to 755 mM.

The controls were done by injecting 0.2 ml of the BSS in an identical manner.

In five separate eyes the experimenters injected 0.1 ml of solution having the above stated concentrations of sucrose into the anterior chamber after withdrawing 0.1 ml of aqueous humor.

The experimenters performed vitrectomy with suction on another group of five eyes with the simultaneous infusion of concentrations of the solution of the present invention having sucrose concentrations ranging from 0.1% to 11.0%. The eyes subsequently followed clinically and, after six weeks, analyzed by histological evaluation.

The topical effects of the various concentrations of the sucrose solution was evaluated by applying different concentrations of solution to the cornea.

It will be appreciated that the inventor have conducted similar analysis of other embodiments of the solution of the present invention containing other oligosaccharides, specifically the dissaccharides maltose and lactose with results similar to those that follow.

Results:

Fundus and ERG (Electroretinogram) Examination:

Both fundus and ERG examinations were taken before administration of sucrose in the vitreous cavity. After the introduction of the sucrose solution into the cavity, fundus and ERG examinations were taken every one week. Data from the ERG was recorded by LKC Technologies UTAS-E2000.

The animals' eyes were dilated and adapted in dark room for 20 minutes. Latency was 5 msec. per division. Amplitude was recorded in uV. Three sweeps were averaged for each step. Five steps were recorded per animal according to a preset program in the computer. Parameter of amplitudes were recorded to explain the ERG changes before and after administration of the sucrose. The ERG chart was stored on the computer and analyzed using a data report software. Data were plotted on a laser printer.

Vessels of the retina were visible under fundus examination after the administration of sucrose into the vitreous cavity.

For each eye, each ERG was assessed in comparison with values of amplitude of ERGs before and after sucrose administration. Recordings of ERG a-wave and b-wave were considered individual differences in both latency and amplitude. Various concentrations of sucrose administered produced no different amplitudes of ERG a-wave and b-wave in most eyes one week after injection. Amplitudes of all eyes recovered in two weeks after sucrose administration when compared with the values of amplitudes that were recorded before administration of the sucrose and one week after sucrose injection. The results of the ERGs suggest that the sucrose solutions caused no damage to the retina.

Slit lamp examination of the cornea and lenses demonstrated no changes. The corneas and the lenses remained clear at all times after injection of the solution of the present invention. Histological exam demonstrated normal structure of the lenses and corneas (see below).

Topical administration of the solution of the present invention containing sucrose did not damage the epithelium and did not cause haziness in the cornea. 2. Histology:

Two weeks after sucrose injection, the rabbits were deeply anesthetized and the eyes were enucleated and fixed in a fixative containing 2% paraformaldehyde and 3% glutadehyde. The animals immediately were killed with an overdose of pentobarbital sodium (Butler Co., Columbus, Ohio). Following the fixing of the eyes, paraffin embedding, sectioning and hematoxylin-eosin stains were taken for retinal histological examination.

A vertical section through the rabbit eye was examined under light microscope. There was normal organization between the cells of layers of the retina. The histologies of outer segments and inner segments, photoreceptor and ganglion cell layers appeared to be normal in comparison with the controls. Therefore, histological findings confirmed that the sucrose solutions did not damage the retina.

Similarly, the lenses, vitreous and the cornea showed normal histological findings. The eyes that underwent vitrectomy also showed normal ocular structures upon histological examination.

Discussion:

An analysis of the above data indicates that a disaccharide solution can be introduced into the vitreous cavity of the eye, injected into the anterior chamber or used topically without causing retinal damage or clouding of the lens or the cornea. The molecular size of the disaccharide and the lack of an active transport mechanism in the cell wall prevents the movement of the disaccharide molecule into the cells. Since there is no enzymes (i.e.sucrase, maltase or lactase) present in the vitreous cavity or anterior chamber, the disaccharide will not be broken down into its component simple sugars. Thus, there will be no by-product glucose, galactose or fructose present to enter the cells and cause clouding or damage. Furthermore, the smaller molecular size of a disaccharide eliminates the problems associated with polysaccharides such as dextrans or methylcellulose which prevented phacoemulsification or irrigation of vitreous blood.

The disaccharide can be added to physiologic solutions containing glucose or other osmotic agents. Since the disaccharide cannot actively enter the cell, it maintains the osmotic pressure of the extracellular fluid and prevents fluid from flowing into the cells. In this way the solution of the present invention prevents swelling of the cells and prevents clouding or haziness of the lens or cornea.

The test results indicate that the disaccharide solution can be used topically with satisfactory results. For example, since the disaccharide cannot pass into the corneal cells, the solution will be an excellent dehydrating solution. Moreover, the solution can be used both topically and in the vitreous as a vehicle for pharmaceutical agents. For example a disaccharide solution containing any one or a combination of antibiotics, antifungals, nonsteroidal antiinflammatories, steroids, anesthetics, vasoconstrictors, or other pharmacological agent is contemplated by the inventor and within the scope of the invention.

It will be appreciated from the foregoing discussion that several changes and modifications may be made in the solution of the present invention without departing from scope of the invention. For example, the solution may be either hypoosmolar or hyperosmolar without departing from the scope of the invention. Therefore, the foregoing specification is intended to be descriptive only and should not be construed in a limiting sense.

I claim:

1. A method of irrigating an ocular cavity during ophthalmologic surgery comprising the steps of:

preparing an ophthalmic solution containing an effective amount of an oligosaccharide to prevent swelling of ocular tissue cells when in contact with said solution, and introducing said ophthalmic solution into said ocular cavity and irrigating said ocular cavity substantially without swelling of ocular tissue cells.

2. The method of claim 1, wherein said ophthalmic solution contains a pharmaceutical agent.

3. The method of claim 2, wherein said pharmaceutical agent is selected from the group consisting of antibiotics, antifungals, nonsteroidal antiinflammatories, steroids, anesthetics, vasoconstrictors and mixtures thereof.

4. The method of claim 1, wherein said oligosaccharide is a disaccharide selected from the group consisting of sucrose, lactose and maltose.

5. The method of claim 1, wherein said ophthalmic solution is a 0.1% to 11.4% disaccharide solution and wherein said method comprises introducing said solution into an intraocular cavity of said eye to irrigate said intraocular cavity without swelling of tissue cells.

6. The method of claim 1, wherein said ophthalmic solution is selected from the group consisting of saline, Lactated Ringers and balanced salt solution.

7. A method of inhibiting osmotic pressure increases in the ocular tissue cells of an eye during ophthalmic surgery comprising the steps of:

preparing an ophthalmic solution containing an effective amount of a disaccharide to inhibit osmotic pressure increases in the ocular tissue cells; and introducing said ophthalmic solution into an ocular cavity of a patient substantially without swelling of ocular tissue cells.

8. The method of claim 7, wherein said ophthalmic solution is a 0.1 to 11.4% aqueous solution of said disaccharide and wherein said method comprises introducing said solution into an intraocular cavity without swelling of ocular tissue cells.

9. The method of claim 8, wherein said disaccharide is selected from the group consisting of sucrose, lactose and maltose.

10. The method of claim 7, wherein said ophthalmic solution is selected from the group consisting of saline, Lactated Ringers and balanced salt solution.

11. The method of claim 7, wherein said ophthalmic solution includes a pharmaceutical agent selected from the group consisting of antibiotics, antifungals, antiinflammatories, steroids, anesthetics, vasoconstrictors and mixtures thereof.

12. A method of introducing a pharmaceutical agent to the eye comprising the steps of:

introducing an ophthalmic solution to the eye of a patient, said solution comprising at least one pharmaceutical agent in a pharmaceutically effective amount and at least one disaccharide in an effective amount to maintain osmotic pressure in extracellular tissue and to inhibit fluid flow into the ocular tissue cells of the eye and inhibit swelling of ocular tissue cells.

13. The method of claim 12, wherein said pharmaceutical agent is selected from the group consisting of antibiotics, antifungals, antiinflammatories, steroids, anesthetics, vasoconstrictors and mixtures thereof.

14. The method of claim 12, wherein said ophthalmic solution is a 0.1 to 11.4% solution of said disaccharide, wherein said disaccharide is selected from the group consisting of sucrose, lactose and maltose and wherein said method comprises introducing said solution into an intraocular cavity of said eye without swelling of tissue cells.

15. The method of claim 12, wherein said ophthalmic solution is selected from the groups consisting of saline, Lactated Ringers and balanced salt solutions.

16. A method of irrigating an intraocular cavity of an eye during intraocular surgery comprising the steps of:

preparing an ophthalmic solution containing a disaccharide in an effective amount to inhibit osmotic pressure increases in ocular tissue cells; and introducing said ophthalmic solution into said intraocular cavity and irrigating said intraocular cavity to maintain osmotic pressure substantially without swelling of ocular tissue cells.

17. The method of claim 16, wherein said intraocular cavity of the eye is the vitreous, anterior and posterior cavity.

18. The method of claim 16, wherein said ophthalmic solution is a 0.1 to 11.4% solution of disaccharide, wherein said disaccharide is selected from the group consisting of sucrose, lactose and maltose.

19. The method of claim 16, wherein said ophthalmic solution is selected from the group consisting of saline, Lactated Ringers and balanced salt solution.

20. The method of claim 16, wherein said ophthalmic solution includes a pharmaceutical agent selected from the group consisting of antibiotics, antifungals, antiinflammatories, steroids, anesthetics, vasoconstrictors and mixtures thereof.

* * * * *